United States Patent
Bennett et al.

(10) Patent No.: US 11,884,904 B2
(45) Date of Patent: Jan. 30, 2024

(54) GAS FERMENTATION USING MULTIPLE-PASS TRICKLE BED REACTORS

(71) Applicant: ICM, Inc., Colwich, KS (US)

(72) Inventors: Albert Bennett, Haven, KS (US); Jonathan N. Orr, Andover, KS (US)

(73) Assignee: ICM, Inc., Colwich, KS (US)

( * ) Notice: Subject to any disclaimer, the term of this patent is extended or adjusted under 35 U.S.C. 154(b) by 0 days.

(21) Appl. No.: 16/642,781

(22) PCT Filed: Aug. 27, 2018

(86) PCT No.: PCT/US2018/048137
§ 371 (c)(1),
(2) Date: Feb. 27, 2020

(87) PCT Pub. No.: WO2019/046188
PCT Pub. Date: Mar. 7, 2019

(65) Prior Publication Data
US 2021/0079326 A1    Mar. 18, 2021

Related U.S. Application Data

(60) Provisional application No. 62/551,074, filed on Aug. 28, 2017.

(51) Int. Cl.
*C12M 1/107* (2006.01)
*C12M 1/00* (2006.01)
(Continued)

(52) U.S. Cl.
CPC .............. *C12M 21/04* (2013.01); *C12M 1/00* (2013.01); *C12M 23/58* (2013.01); *C12M 25/02* (2013.01);
(Continued)

(58) Field of Classification Search
CPC ........ C12M 21/04; C12M 1/00; C12M 23/58; C12M 25/20; C12M 29/18; C12R 1/01; C12R 2001/01
(Continued)

(56) References Cited

U.S. PATENT DOCUMENTS

| 5,869,541 | A | 2/1999 | Euzen et al. |
| 7,322,193 | B2 * | 1/2008 | Bering ................... F02M 26/06 60/605.2 |

(Continued)

FOREIGN PATENT DOCUMENTS

| CN | 101279229 B | * | 2/2011 |
| CN | 101279229 B | | 2/2011 |

(Continued)

OTHER PUBLICATIONS

CN101279229B Machine English Translation (Year: 2011).*
(Continued)

*Primary Examiner* — Michael L Hobbs
*Assistant Examiner* — Lenora A Abel
(74) *Attorney, Agent, or Firm* — Schwegman Lundberg & Woessner, P.A.

(57) ABSTRACT

The subject matter of this application is using novel biological reactors for the fermentation of gases into liquid products. More specifically, the subject matter relates to the use of a Multiple-Pass Trickle Bed Reactor (MP-TBR) for the anaerobic or aerobic and biological fermentation of gases generated from industrial processes and/or from the gasification of biomass and other organic carbon sources. The products may include, but are not limited to, ethanol and other valuable chemicals.

16 Claims, 4 Drawing Sheets

(51) Int. Cl.
*C12M 1/12* (2006.01)
*C12N 1/20* (2006.01)
*C12R 1/01* (2006.01)

(52) U.S. Cl.
CPC ............ *C12M 29/18* (2013.01); *C12N 1/205* (2021.05); *C12R 2001/01* (2021.05)

(58) Field of Classification Search
USPC ...................................................... 435/296.1
See application file for complete search history.

(56) References Cited

U.S. PATENT DOCUMENTS

| | | | | |
|---|---|---|---|---|
| 8,759,047 | B2* | 6/2014 | Datta | .................... C07C 53/124 |
| | | | | 435/161 |
| 8,945,372 | B2* | 2/2015 | Dindi | .................... C10G 65/02 |
| | | | | 208/59 |
| 2010/0261242 | A1* | 10/2010 | Harvey | .................... C12P 19/02 |
| | | | | 435/157 |
| 2016/0068868 | A1* | 3/2016 | Davis | ........................ C12P 7/06 |
| | | | | 435/165 |

FOREIGN PATENT DOCUMENTS

| | | |
|---|---|---|
| CN | 103695024 A | 4/2014 |
| CN | 106563394 A | 4/2017 |
| WO | WO-2013039664 A1 | 3/2013 |
| WO | WO-2015181698 A2 * | 12/2015 ............ B01D 53/84 |
| WO | WO-2015181698 A2 | 12/2015 |

OTHER PUBLICATIONS

International Application Serial No. PCT/US2018/048137, International Search Report dated Nov. 30, 2018, 4 pgs.

International Application Serial No. PCT/US2018/048137, Written Opinion dated Nov. 30, 2018, 6 pgs.

International Application Serial No. PCT/US2018/048137, International Preliminary Report on Patentability dated Mar. 12, 2020, 8 pgs.

* cited by examiner

GAS FERMENTATION USING MULTIPLE-PASS TRICKLE BED REACTORS

CROSS REFERENCE TO RELATED APPLICATION

This application is a U.S. National Stage Filing under 35 U.S.C. 371 from International Application No. PCT/US2018/048137, filed on Aug. 2, 2018, and published as WO 2019/046188 A1 on Mar. 7, 2019, which claims the benefit of priority to U.S. Provisional Application No. 62/551,074, entitled "Gas Fermentation Using Multiple-Pass Trickle Bed Reactors," filed on Aug. 28, 2017, the content of each of which is hereby incorporated by reference in its entirety.

TECHNICAL FIELD

The subject matter of this disclosure relates to the use of biological reactors for the fermentation of gases into liquid products, such as ethanol and other valuable chemicals. More specifically, the subject matter relates to the use of a Multiple-Pass Trickle Bed Reactor (MP-TBR) for the anaerobic or aerobic and biological fermentation of gases generated from industrial processes and/or from the gasification of biomass and other organic carbon sources.

BACKGROUND

The energy demand on the world is expected to increase by 40% or more by 2035 due to the increase in global population. There is a need to reduce emissions association with fuel consumption. The challenges are to increase the amount of energy to meet the demand, while minimizing carbon emissions to protect the environment at the same time. Anaerobic fermentation of gases is a technology that could help as it may possible qualify for low carbon fuel standards and commodity chemical synthesis. However, widespread application of the anaerobic fermentation of gases generated from industrial processes and/or commercial scale gasification has been limited. This is in part due to the very high capital costs and energy requirements associated with the utilization of currently available bio-reactor technologies.

Continuously Stirred-Tank Reactors (CSTRs) or Bubble Reactors (BRs), which are two technologies known in the industry, have typically been utilized by the limited number of actual commercial-scale projects that have been developed. CSTRs and BRs are usually liquid filled pressurized vessels. Due to their tall height requirements, CSTRs and BRs typically require significant levels of gas compression, anywhere from 30 psi to 50 psi (or more) above atmospheric conditions, in order to serve as anaerobic fermentation reactors. The primary disadvantages associated with gas compression are high power requirements, high capital costs and high maintenance requirements. CSTRs also require agitation systems further adding to equipment costs, power requirements and system maintenance.

Gasification of biomass or other high carbon fuel sources yield fermentable gas products with major components typically comprised of varying levels of carbon monoxide (CO), hydrogen ($H_2$), carbon dioxide ($CO_2$), methane ($CH_4$) and nitrogen ($N_2$). Carbon monoxide and hydrogen are the principle gases of interest that may be needed to support most microbes used in anaerobic fermentation processes. In general terms, gasification can utilize either indirect heating or autothermic processes to generate product gases. Commercial-scale indirect gasification systems have found limited application due to difficulties in scaling to larger industrial applications.

Autothermic gasification systems are readily scalable and can use either oxygen-blown or air-blown technologies. The principle advantage of air-blown gasification systems (that operate at near atmospheric conditions) is that they can be less expensive to build and operate. The disadvantage of air-blown gasification, when considering gas fermentation in CSTRs and BRs, is that the resulting gasification products (i.e., Producer Gas) are high in nitrogen content (50%-55% volume), which greatly increases capital and energy costs associated with gas compression. The use of high nitrogen Producer Gases can also add costs to CSTRs and BRs due to the need for larger reactor volumes. As a result, CSTR and BR approaches are generally considered with oxygen-blown gasification platforms to provide product gases (i.e., Syngas) that are relatively low in nitrogen content (2%-3% volume). The use of oxygen, however, requires very significant levels of additional capital and energy costs necessary for procurement and operation of oxygen generation equipment.

Trickle Bed Reactors (TBRs) are known in industry and have been applied in many laboratory studies demonstrating biological fermentation of both Producer Gas and Syngas. They are typically comprised of a reactor vessel filled with solid media that has a large associated surface area and void volume. Liquid fermentation broth is continuously recirculated and distributed at the top of solid media bed and as the liquid fermentation broth flow by gravity to the bottom of the reactor vessel. Gases are typically introduced and circulated countercurrent to liquid flow. Co-current liquid-gas configurations are also feasible and have been demonstrated in laboratory studies. The large surface area and void volume contained in the trickle bed promote turbulent gas flow through the bed and facilitate mass transfer of CO and $H_2$ into the liquid fermentation broth. Typical TBR applications employ a single pass of gases through solid media, which is used for laboratory scale studies. However, the disadvantage to single-pass TBRs is that they do not scale well to industrial and commercial applications.

Accordingly, there is a need for the Multiple-Pass Trickle Bed Reactor because of its significant potential for reducing capital and energy requirements associated with the commercial scale anaerobic or aerobic fermentation of gases.

SUMMARY

The subject matter comprises a method and apparatus for the biological fermentation of gases which employs a modified trickle bed reactor that has internal sectioning that allows for multiple-pass configuration of fermentable gases through multiple media bed sections contained within the same reactor vessel. The multiple-pass TBR configuration allows for a significant increase in recirculating gas velocities and turbulence within the media bed at near-atmospheric pressures (I psig). The ability to increase gas velocities within the media bed greatly improves the potential for mass transfer to the fermentation broth.

There is a method that includes providing anaerobic conditions in a single or multiple-stage process for production of alcohols, acids and/or other potentially valuable metabolic by-products, from the biological fermentation of gases generated by industrial processes and/or the gasification of organic materials by using a multiple-pass trickle reactor with an organism.

There is a device used to carry out biological fermentation processes in a production facility comprising a multiple-pass trickle bed reactor providing anaerobic conditions for production of alcohols, acids and/or metabolic by-products, from the biological fermentation of gases generated by industrial processes and/or the gasification of organic materials.

There is a device used to carry out biological fermentation processes in a production facility comprising a multiple-pass trickle bed reactor providing aerobic conditions for production of alcohols, acids and/or metabolic by-products, from the biological fermentation of gases generated by industrial processes and/or the gasification of organic materials.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. Other aspects and advantages of the claimed subject matter will be apparent from the following Detailed Description of the embodiments and the accompanying figures.

BRIEF DESCRIPTION OF THE DRAWINGS

The Detailed Description is set forth with reference to the accompanying figures. In the figures, the left-most digit(s) of a reference number identifies the figure in which the reference number first appears. The use of the same reference numbers in different figures indicates similar or identical items. The features illustrated in the figures are not necessarily drawn to scale, and features of one embodiment may be employed with other embodiments as the skilled artisan would recognize, even if not explicitly stated herein.

DETAILED DESCRIPTION

The Detailed Description explains embodiments of the subject matter and the various features and advantageous details more fully with reference to non-limiting embodiments and examples that are described and/or illustrated in the following attached description and accompanying figures. Descriptions of well-known components and processing techniques may be omitted so as to not unnecessarily obscure the embodiments of the subject matter. The examples used herein are intended merely to facilitate an understanding of ways in which the subject matter may be practiced and to further enable those of skill in the art to practice the embodiments of the subject matter. Accordingly, the examples, the embodiments, and the figures herein should not be construed as limiting the scope of the subject matter.

The subject matter comprises methods and apparatus for the biological fermentation of gases. Advantages of this method and apparatus are that they do not require high pressure gas compressors, oxygen generation equipment and/or pressurized reactor vessels. The subject matter employs a multiple-pass trickle bed reactor (MP-TBR) that has internal sectioning to allow for multiple-pass configuration of fermentable gases through multiple media bed sections contained within one reactor vessel. When compared to traditional single pass TBR, the MP-TBR configuration allows for a significant increase in recirculating gas velocities and turbulence within the media bed at near-atmospheric pressures (psig). The ability to increase gas velocities within the media bed greatly improves the potential for mass transfer to the fermentation broth, which in turn can allow for the practical use of Producer Gases (or other industrial waste gases) that contain high levels of nitrogen and other inert components. For example, the MP-TBR ferments gases into liquid products, such as ethanol, butanol, acetic acid, butyric acid, methane, methanol, ammonia, other valuable chemicals, other valuable metabolic by-products, and the like.

Illustrative Environment

Figure 1:
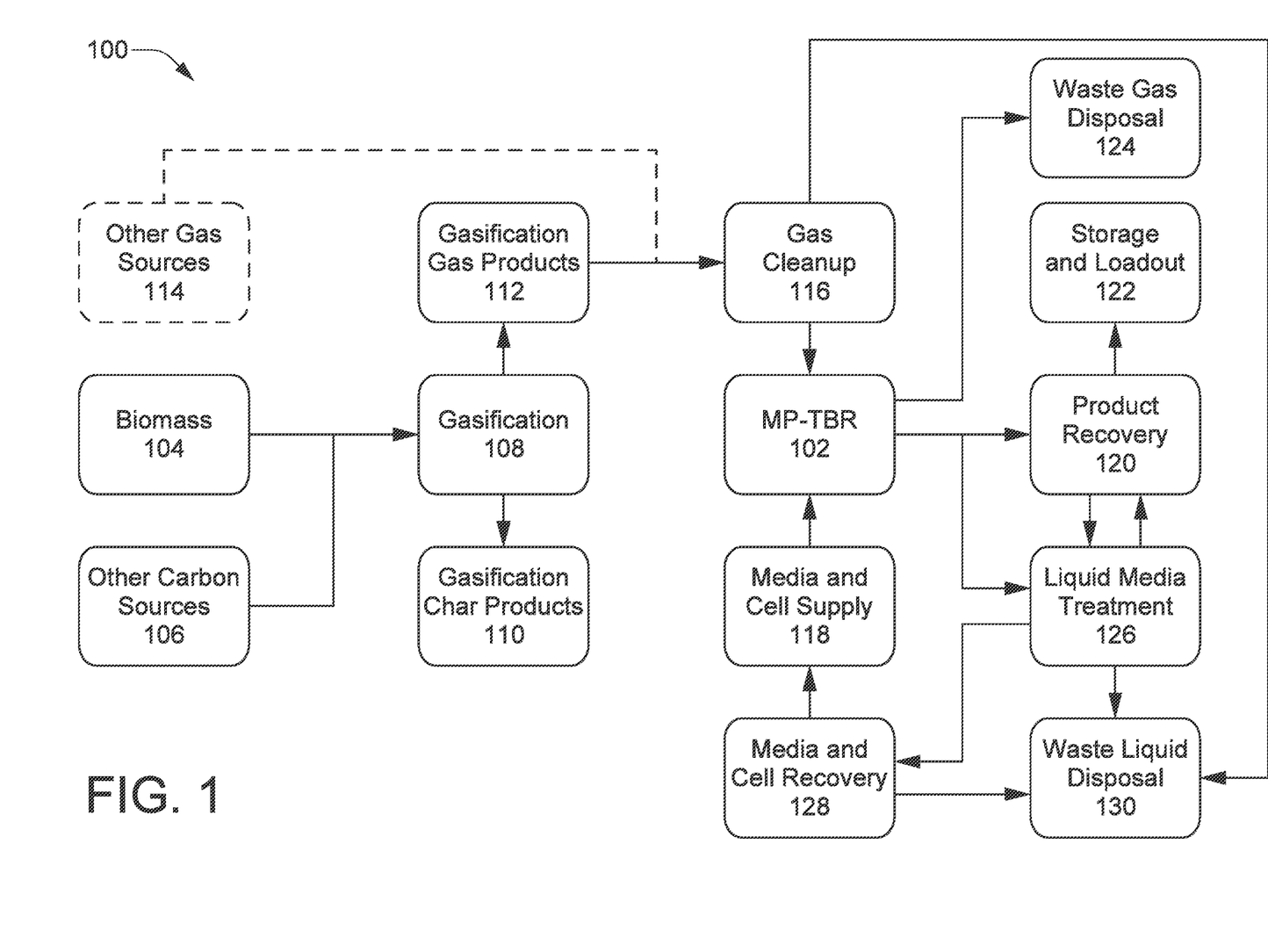
FIG. 1 illustrates an example environment for a production facility using a MP-TBR.

FIG. 1 illustrates a flow diagram showing an example environment of a production facility 100 that may incorporate Multiple-Pass Trickle Bed Reactors (MP-TBR) 102. The production facility 100 shows the process may send biomass 104 and/or other carbon sources 106 to gasification 108. Gasification 108 is a process that generates solid gasification char products 110 and gasification gas products 112. Other gas sources 114 can be used to supplement or completely replace gasification gas products 112. The process sends the gasification gas products 112 to gas cleanup 116, prior to utilization of the gasification gas products 112 and/or other gas sources 114 in anaerobic fermentation processes, such as MP-TBR 102. Anaerobic processes do not require oxygen. However, aerobic fermentation processes may also be used.

Cleaned gas products coming from the gas cleanup 116 module and/or liquid media and cell supply 118 are supplied to the MP-TBR 102 on a continuous or batch basis. The media and cell supply 118 may include but is not limited to organisms, bacteria, and the like that help convert the gas into useful products, fuel and chemicals. The anaerobic fermentation process generated in the MP-TBR 102 creates valuable products that are delivered to product recovery 120 systems and product storage and loadout 122 systems.

The MP-TBR 102 also generates waste gases that are delivered to waste gas disposal 124 systems. A portion of liquid media and product contained in the MP-TBR 102 can be delivered directly to product recovery 120 systems or go through liquid media treatment 126. Liquid media treatment 126 can generate liquid streams with valuable products going to product recovery 120. The products generated may include, but are not limited to, ethanol, butanol, acetic acid, butyric acid, methane, methanol, ammonia, other valuable chemicals, other valuable metabolic by-products, and the like. Liquid media treatment 126 can generate liquid streams that go to media and cell recovery 128, which in turn supplements media and cell supply 118 to the MP-TBR 102. Waste liquid disposal 130 is utilized for waste products generated in media and cell recovery 128 and liquid media treatment 126 equipment.

Illustrative Equipment

Figure 2:
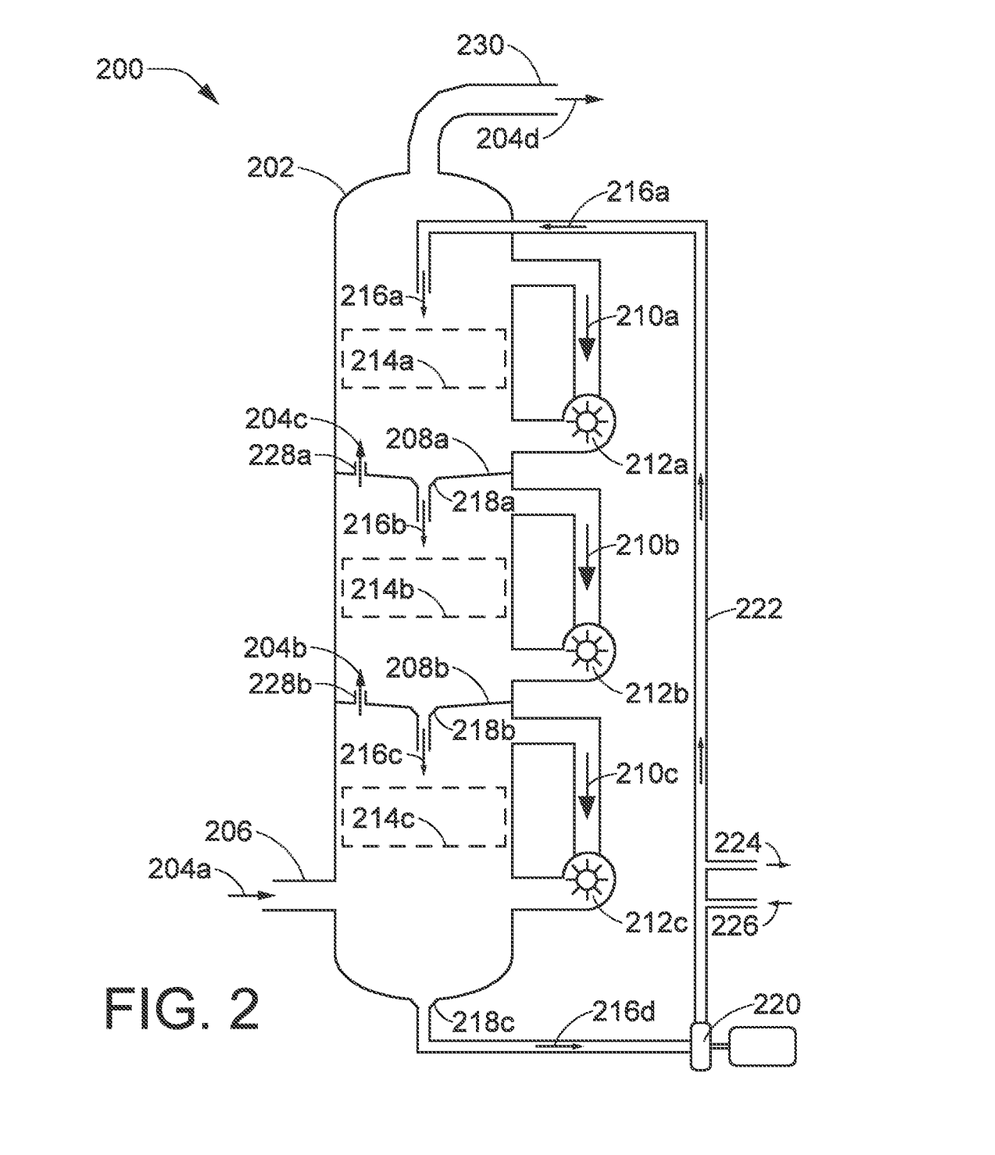
FIG. 2 illustrates a schematic of a single vertical reactor with MP-TBR, according to one example.

FIG. 2 illustrates a vertical reactor schematic of a MP-TBR system 200 according to one example. System 200 is comprised of a single vertically configured fermentation reactor vessel 202 having a gas supply 204(a) delivered to the reactor inlet 206 near the base of reactor vessel 202. The gas supply 204(a) feedstock, may include, but is not limited to, gases generated from any industrial processes and/or commercial scale gasification. The gas supply 204(a) may include industrial or waste gases, industrial off-gases, syngas, or gases generated from agricultural residues, biomass, refuse derived fuels, and the like. The gas supply are usually rich in components, such as CO, $H_2$ and/or $CO_2$. As an example, the reactor vessel 202 shown is divided into three sections, separated by an internal liquid and gas barrier 208(a), (b). The reactor vessel 202 may have any number of sections, ranging from two to sixteen sections. The sections may include packing materials in some embodiments. As the inlet gas 204(a) travels through the vessel reactor 202, gas 204(b), (c), (d) composition will be modified by and/or during the fermentation process.

The reactor vessel 202 is divided into three section with the bottom section located near the inlet gas supply 204(a). Each section has a large volume flow of recirculation gas 210(a), (b). (c) generated by a gas recirculation fan 212(a), (b), (c). As shown, the recirculation gases 210(a), (b), (c) are generated by their respective gas recirculation fans 212(a), (b), (c). Each section has packing material 214(a),(b), (c) that provides surface area to promote mass transfer between liquid fermentation broth 216(a), (b), (c), (d) and recirculating gases 210(a), (b), (c) as they flow countercurrent through packing material 214(a), (b), (c). The packing material may include but is not limited to catalyst particles. As liquid fermentation broth 216(a), (b), (c), (d) travel through each reactor section; microbe, nutrient, metabolite and dissolved gas concentrations will be modified by the active fermentation process.

Liquid collection 218(a), (b), (c) is located on each barrier 208(a), (b) and at the bottom of reactor vessel 202. Liquid fermentation broth 216(a) is recirculated to the top of reactor vessel 202 by a pump 220 by way of liquid recirculation circuit 222. A portion of fermentation broth 224 can be removed for further processing and recovery of valuable metabolic products. Liquid media makeup and/or recovered microbes 226 can be introduced into the reactor vessel 202 by way of liquid recirculation circuit 222.

As additional inlet gas supply 204(a) enters the reactor vessel 202, a fraction of the first and second section's recirculating gas 204(b), (c) is forced into the next section through a gas port 228(a), (b) located in the liquid and gas 208(a), (b) barrier. As additional inlet gas supply 204(a) enters the reactor vessel 202, a fraction of the recirculating gas in the third section is removed as outlet gas flow 204(d), shown at top of the reactor vessel 202 through a gas outlet 230.

There may be co-current or counter-current movement of the liquid and the gas over packing material. That is, all downward in co-current or downward and upward in counter-current. Embodiments include, but are not limited to, single vertical reactors that can range from about two to about sixteen sections. An embodiment might include, but is not limited to a single vertical reactor with six sequentially positioned sections each with associated packing and gas recirculation fans. In an embodiment, a single vertical reactor may include three sequentially positioned sections, as shown in FIG. 2. An embodiment may include a single vertical reactor with a single section.

The liquid media makeup and or recovered microbes 226 may include organisms. Possible organisms that may be used in gas fermentation include, but are not limited to, bacteria, yeast, such as acetogens. The acetogens may include but are not limited to, *Clostridium ljlungdahlii Clostridium autoethanogenum, Eurobacterium limosum, Clostridium carboxidivorans, Peptostreptococus products,* and *Butyribacterium methylotrop.* Other types of organisms are possible to ferment the gas supply. Other possible microorganisms include, but not limited to, bacteria species of *Clostridium, alklibaculum, Escherichia, Zymomonas, Rhodospirillum* and *Rhodopseudomonas*; or other organisms such as yeast, blue green algae and green algae.

Figure 3:
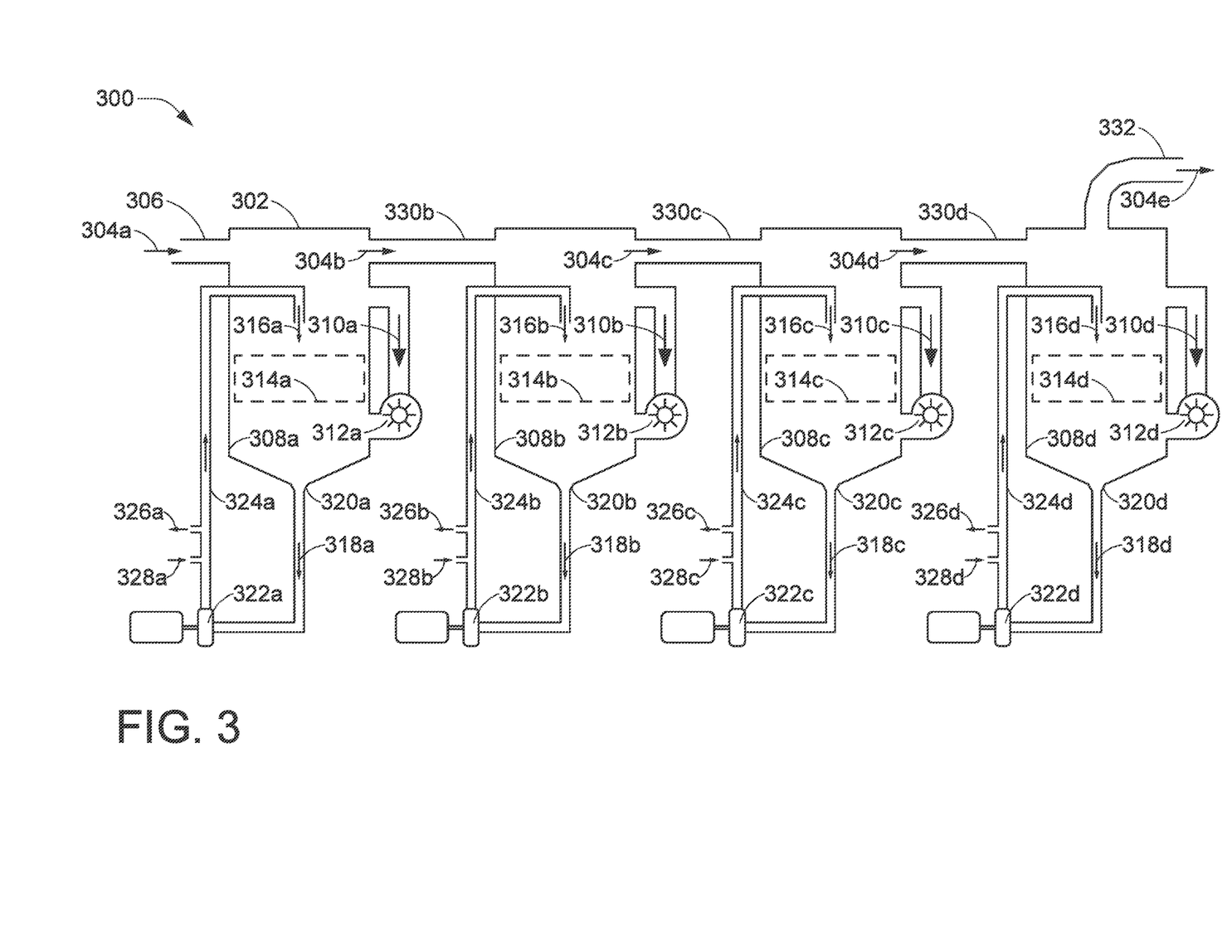
FIG. 3 illustrates a schematic of a horizontal system with MP-TBR according to one example.

FIG. 3 is similar to FIG. 2, except this figure illustrates an embodiment of a horizontal reactor. FIG. 3 illustrates a horizontal reactor schematic of a MP-TBR system 300 according to one example. System 300 is comprised of a single horizontal configured fermentation reactor vessel 302 having a gas supply 304(a) delivered to the reactor inlet 306. The reactor vessel 302 is divided four sections (as illustrated, but can have fewer or more) by an internal liquid and gas barrier 308(a), (b), (c). (d). Each section has a large volume flow of recirculation gas 310(a), (b), (c), (d) generated by a gas recirculation fan 312(a), (b), (c), (d). Each section has packing material 314(a), (b), (c), (d) that provides surface area to promote mass transfer between liquid fermentation broth 316(a), (b), (c). (d) and recirculating gas 310(a), (b), (c), (d) as they flow countercurrent through packing 314(a), (b), (c), (d). As liquid fermentation broth 316(a), (b), (c), (d) travel through corresponding reactor sections; microbe, nutrient, metabolite and dissolved gas concentrations in 318(a), (b), (c), (d) will be modified by the active fermentation process. Liquid collection 320(a), (b), (c), (d) is located at the bottom of each of the four sections of reactor vessel 302.

In each section a separate pump 322(a), (b). (c), (d) are used to recirculate liquid fermentation broth 318(a), (b), (c). (d) by way liquid recirculation circuits 324(a), (b), (c), (d). A portion of fermentation broth 326(a), (b), (c), (d) can be removed for further processing and recovery of valuable metabolic products. Liquid media makeup and/or recovered microbes 326(a), (b), (c), (d) can be introduced into reactor vessel 302 by way of liquid recirculation circuits 324(a), (b), (c), (d). A portion of the recirculated liquid 326(a), (b), (c), (d) can be passed to the next stage in countercurrent fashion or drawn off depending on the concentration achieved and the preferred method of operation. As inlet gas 304(a) enters reactor vessel 302 a fraction of the first, second and third section's recirculating gas 304(b), (c), (d) is forced into the next section by an internal passage 330(b), (c), (d) located between each section. As inlet gas 304(a) enters reactor vessel 302 a fraction of the recirculating gas in the fourth section is removed as outlet gas flow 304(e) via reactor vessel 302 gas outlet 332. As the inlet gas 304(a) travels through the reactor, gas 304(b), (c), (d), (e) composition will be modified by the fermentation process.

The single-horizontally configured reactor vessel may include, two to sixteen sequentially positioned sections, each with associated packing and gas recirculation fans. An embodiment might include, but is not limited to a single horizontally configured reactor vessel with four sequentially positioned sections each with associated packing and gas recirculation fan as shown in FIG. 3.

Figure 4:
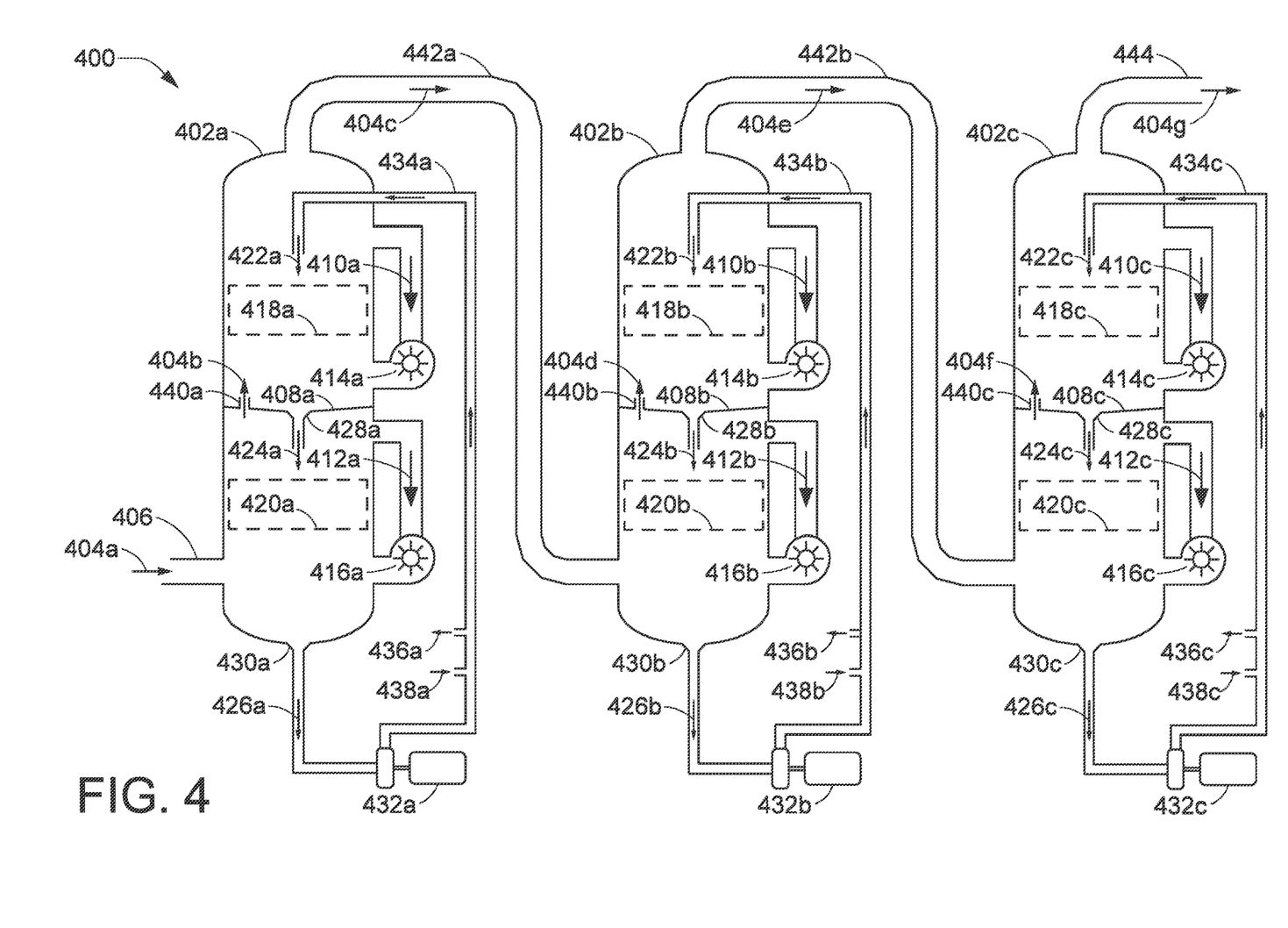
FIG. 4 illustrates a schematic of a series of vertical reactors with MP-TBR in a system according to one example.

FIG. 4 is similar to FIG. 2, except this figure illustrates an embodiment of a series of reactors. Details that are not similar to FIG. 2 will be discussed below with reference to FIG. 4. FIG. 4 illustrates a series of reactors schematic of a MP-TBR system 400 according to one example. In an embodiment, a system 400 is comprised of three sequentially configured fermentation reactor vessels 402(a),(b), (c) having a gas supply 404(a) delivered to the reactor inlet 406 located near the base of reactor vessel 402(a). The reactor vessels 402(a), (b), (c) are each divided into two sections by an internal liquid and gas barrier 408(a), (b), (c). The upper section has a large volume flow of recirculation gas 410(a), (b), (c) generated by a gas recirculation fan 414(a), (b), (c). The bottom section has a large volume flow of recirculation gas 412(a), (b). (c) generated by a gas recirculation fan 416(a), (b), (c). The upper and bottom sections have respective packing material 418(a), (b), (c) and 420(a), (b), (c) that provides surface area to promote mass transfer between liquid fermentation broth 422(a), (b), (c); 424(a), (b), (c); 426(a), (b), (c) and recirculating gas 410(a), (b), (c); 412(a), (b), (c) as they flow countercurrent through packing 418(a), (b), (c); 420(a), (b), (c).

As liquid fermentation broth 422(a), (b), (c); 424(a), (b), (c); 426(a), (b), (c) travel through corresponding reactor sections; microbe, nutrient, metabolite and dissolved gas concentrations will be modified by the active fermentation process. Liquid collection 428(a), (b), (c) is located on each barrier 408(a), (b), (c). Liquid collection 430(a), (b), (c) is located at the bottom of reactors 402(a). (b), (c). Liquid fermentation broth 422(a), (b), (c) is recirculated to the top of reactors 402(a), (b), (c) by pumps 432(a), (b), (c) by way liquid recirculation circuits 434(a), (b), (c). A portion of fermentation broth 436(a), (b), (c) can be removed for further processing and recovery of valuable metabolic products. Liquid media makeup and/or recovered microbes 438 (a), (b). (c) can be introduced into reactor vessels 402(a), (b), (c) by way of liquid recirculation circuits 434(a), (b), (c). A portion of the recirculated liquid 436(a), (b), and/or (c) can be passed to the next stage in countercurrent fashion or drawn off depending on the concentration achieved and the preferred method of operation. As inlet gas 404(a) enters the reactor 402(a) a fraction of the bottom section's recirculating gas 404(b), (d), (f) is forced into the subsequent upper sections through gas port 440(a), (b), (c) located in the barrier 408(a), (b), (c). As inlet gas 404(a) enters the reactor 402(a) a fraction of the upper section's recirculating gas 404(c), (e) is forced into connecting ducting 442(a), (b) located between reactors 402(a), (b), (c). As inlet gas 404(a) enters reactor 402(a) a fraction of the recirculating gas in the upper section of reactor 402(c) is removed as outlet gas flow 404(g) via reactor vessel 402(c) gas outlet 444. As the inlet gas 404(a) travels through the reactor, gas 404(b), (c), (d), (e), (f), (g) composition will be modified by the fermentation process.

Embodiments include, but are not limited to, two to ten reactor vessels connected in series by ducting, with each vertical reactor vessel containing two to sixteen sequentially positioned sections, each with associated packing and gas recirculation fans. An embodiment might include, but is not limited to three vertically configured reactor vessels connected in series by ducting, with each vertical reactor vessel containing two sequentially positioned sections each with associated packing and gas recirculation fan, as shown in FIG. 4.

Embodiments include but are not limited to, two or more reactors in a series or in a parallel configuration. As an example, there may be three as shown in a series. As discussed previously, there may only be a single reactor, either vertical or horizontal.

Operating parameters for the reactor vessels, include but are not limited to, near-atmospheric pressure (+/−3 lbs per sq inch), temperatures ranging from 45° F. to 140° F. and liquid media pH ranging from 2 to 12. Other embodiments include, but are not limited to operations, at pressures ranging between 1 and 12 psia or between 17 and 115 psia, operating temperatures as low as 70° F. or as high as 140° F. and pH between 2 and 4 or pH between 6 and 12.

Operating conditions may be anaerobic or aerobic, depending on organisms. The types of organisms were described with reference to FIG. 2, but may be applied in any of these types of reactors.

Compositions of reactor vessel, packing materials, and interconnecting ducting and piping may include, but are not limited to, stainless steel, plastic or other corrosion resistant materials.

Liquid medium includes, but is not limited to, essential nutrients, vitamins, minerals and other components necessary to support microorganisms and production of valuable metabolic co-products and/or biomass. One embodiment might include, but not limited to, about 2 to about 20 gpm per sq. ft of liquid loading to the trickle beds, with microorganism biomass comprising from about 0.5% to about 15% weight of the liquid media (fermentation broth).

Another embodiment might include, but is not limited to, batch or continuous operations.

Operating parameters include, but are not limited to, normal atmospheric pressure +/−3 lbs per sq inch. Other embodiments include vacuum ranging from about 6 psia to about 14 psia. The gas in or gas out is based on pressure or flow measurements. The liquid media or fermentation broth can be based on pH, product concentration, density, optical measurements, temperature, cell counts, and the like.

Operating conditions may be anaerobic or aerobic, depending on the organisms. The time in the reactor for the gas may range from approximately 10 seconds to approximately 60 minutes. The time for the liquid media in the reactor may range from approximately 500 minutes to approximately 1 year. However, on a regular basis a portion of liquid media containing valuable metabolic co-product and microorganism biomass can be removed for further processing, including but not limited to, product recovery, biomass recovery and/or replacement and liquid media replenishment with nutrients, minerals, vitamins and other components necessary to maintain the process in a continuous manner.

The device comprises a biological reactor having a single vessel, or multiple vessels configured in series. A typical operating pressures of 1 psig; operations at pressures less than −1 psig or greater than +1 psig are feasible.

The device has a single gas inlet end where fermentable gases are injected into a reactor, and a single gas outlet end where unused fermentable gases and gaseous fermentation by-products are exhausted from the reactor. The device can be comprised of a reactor with a single vessel that contain a single internal subsection or the reactor can be comprised of a single vessel that contains multiple internal subsections that are configured in series.

The device can be comprised of a reactor with multiple vessels configured in series; each vessel can contain a single internal subsection or each vessel can contain multiple internal subsections that are configured in series.

Each vessel contains a liquid recirculation circuit that supplies liquid fermentation broth to the top of the vessel; liquid is distributed and flows by gravity through the vessel's single or multiple subsections, until liquid reaches the bottom of the vessel where it is delivered to the liquid recirculation circuit.

Each reactor subsection contains a trickle bed comprised of random or structural packing where liquid fermentation broth is distributed over the top of the trickle bed and flows by gravity over the bed's packing materials; liquid loading typically range from 2 to 12 gpm per square foot; liquid loading to each trickle bed can be less than 2 gpm per square foot or greater than 12 gpm per square foot.

Each reactor subsection contains a gas recirculation fan; recirculation fan inlet and outlet can be configured for either countercurrent or co-current liquid-gas flow through the subsection's trickle bed; typical gas recirculation flow rates can range from 2× to 10× the volumetric flow of gases supplied to the reactor: gas recirculation flow rates can be less than 2× or greater than 10× the volumetric flow of gases supplied to the reactor.

Each reactor subsection contains a liquid-gas barrier, liquid is collected by the barrier and delivered to next subsection or delivered to the inlet to the liquid recirculation circuit located at the bottom of the vessel; a portion of each subsection's recirculating gas passes through a gas port located in the liquid-gas barrier or passes through ducting between reactor vessels.

For reactors with multiple vessel configurations, each vessel can have a dedicated pump system supplying the vessel's liquid recirculation circuit; or all collected liquid exiting each vessel can be connected to a manifold supplying a single pump system that distributes liquid to each vessel's liquid recirculation circuit; or a fraction of the total number of reactor vessels can be connected to a manifold supplying a single pump system which distributes liquid to each corresponding reactor vessel liquid recirculation circuits.

A portion of the flow in a recirculation circuit of a first particular vessel can be removed for further processing and recovery of valuable metabolic products.

A portion of the flow in a recirculation circuit of a first particular vessel can be removed and delivered to other particular vessels or subsections that comprise a reactor.

Makeup of liquid media and recovered microbes can be delivered into a liquid recirculation circuit of a particular vessel. Liquid loading to trickle beds contained in a particular vessel can be varied in accordance to vessel location in a multiple-vessel reactor. For, example higher recirculating liquid flow rates can be utilized to improve mass transfer in later vessels as CO and H2 levels are depleted.

Gas recirculation within a particular trickle bed of a particular subsection can be varied in accordance to subsection location within a reactor. For, example higher recirculating gas flow rates can be utilized to improve mass transfer in later subsections as CO and H2 levels are depleted.

Although the subject matter has been described in language specific to structural features and/or methodological acts, it is to be understood that the subject matter defined in the appended claims is not necessarily limited to the specific features or acts described. Rather, the specific features and acts are disclosed as example forms of implementing the claims.

What is claimed is:

1. A device used to carry out biological fermentation processes in a production facility comprising:
   a multiple-pass trickle bed reactor for production of alcohols, acids and/or metabolic by-products, based on the biological fermentation of gases generated by industrial processes or the gasification of organic materials, the multiple-pass trickle bed reactor comprising multiple vessels with at least one vessel having at least one section, and further wherein the sections of the reactor include a first section and a second section separated by a liquid-gas barrier and wherein the sections are arranged sequentially,
   a liquid recirculation circuit that removes liquid fermentation broth from a bottom of the reactor and supplies the fermentation broth to a top of the reactor to be flowed back through the reactor, and
   a first gas recirculation circuit that recirculates gases within the first section and a second gas recirculation circuit that recirculates gases within the second section, wherein the first gas recirculation circuit and the second gas recirculation circuit each provides gas recirculation flow rates that range from 2× to 10× a volumetric flow of gases supplied to the reactor.

2. The device of claim 1, wherein the multiple-pass trickle bed reactor is operatable at a pressure of ±1 psig.

3. The device of claim 1, wherein the multiple-pass trickle bed reactor comprises:
   a single gas inlet end to inject fermentable gases, and a single gas outlet end to exhaust unused fermentable gases and gaseous fermentation by-products from the multiple-pass trickle bed reactor.

4. The device of claim 1, wherein the fermentation broth supplied to the top of the reactor by the liquid recirculation circuit is distributed and flows by gravity through the reactor.

5. The device of claim 1, wherein the multiple-pass trickle bed reactor comprises of random or structural packing with the liquid fermentation broth distributed over a top of the multiple-pass trickle reactor and flows by gravity over the multiple-pass trickle bed reactor's packing materials.

6. The device of claim 1, wherein each section of the multiple-pass trickle bed reactor comprises a gas recirculation fan, a recirculation fan inlet and an outlet.

7. The device of claim 1, wherein
   liquid is collected by the liquid-gas barrier and delivered to a section or delivered to an inlet to the liquid recirculation circuit.

8. The device of claim 1, further including a gas port located in the liquid-gas barrier between the first section and the second section or includes a duct between the first section and the second section.

9. The device of claim 1, wherein the liquid recirculation circuit comprises a pump system.

10. The device of claim 1, wherein the multiple-pass trickle bed reactor comprises a portion of flow of another multiple-pass trickle bed reactor's liquid recirculation circuit, to be removed for further processing and for recovery of products.

11. The device of claim 1, wherein the multiple-pass trickle bed reactor comprises a portion of a flow of another multiple-pass trickle bed reactor's liquid recirculation circuit, to be removed and to be delivered to other multiple-pass trickle bed reactors or subsections that comprise a reactor.

12. The device of claim 1, wherein the liquid fermentation broth removed by the liquid recirculation circuit comprises liquid media and recovered microbes.

13. The device of claim 1, comprising liquid loading to trickle beds contained in the multiple-pass trickle bed reactor, to be varied in accordance to the multiple-pass trickle bed reactor location in a multiple-pass trickle bed reactor.

14. The device of claim 1, wherein gas recirculation by the gas recirculation circuit varies based on subsection location within the multiple-pass trickle bed reactor.

15. The device of claim 1, wherein the multiple-pass trickle bed reactor provides aerobic conditions.

16. A method comprising:
   providing a single or multiple-stage process for production of alcohols, acids and/or other potentially valuable metabolic by-products, from biological fermentation of gases generated by industrial processes and/or gasification of organic materials by using a multiple-pass trickle reactor comprising an organism, the multiple-pass trickle bed reactor comprising multiple vessels with at least one vessel having at least one section, and further wherein the sections of the reactor include a first section and a second section separated by a liquid-gas barrier and wherein the sections are arranged sequentially, the reactor including the organism, removing liquid fermentation broth from a bottom of the reactor and supplying the fermentation broth to a top of the reactor using a liquid recirculation circuit, and recirculating gases within the first section using a first gas recirculation circuit and recirculating gases within the second section using a second gas recirculation circuit, wherein the first gas recirculation circuit and the second gas recirculation circuit each provides gas recirculation flow rates that range from 2× to 10× a volumetric flow of gases supplied to the reactor.

\* \* \* \* \*

UNITED STATES PATENT AND TRADEMARK OFFICE
CERTIFICATE OF CORRECTION

PATENT NO. : 11,884,904 B2
APPLICATION NO. : 16/642781
DATED : January 30, 2024
INVENTOR(S) : Bennett et al.

Page 1 of 1

It is certified that error appears in the above-identified patent and that said Letters Patent is hereby corrected as shown below:

In the Claims

In Column 10, Line 10, in Claim 3, after "and", insert a linebreak

Signed and Sealed this
Fourth Day of March, 2025

Coke Morgan Stewart
*Acting Director of the United States Patent and Trademark Office*